(12) United States Patent
Receveur et al.

(10) Patent No.: US 12,133,724 B2
(45) Date of Patent: Nov. 5, 2024

(54) MACHINE VISION TO PREDICT CLINICAL PATIENT PARAMETERS

(71) Applicant: Hill-Rom Services, Inc., Batesville, IN (US)

(72) Inventors: Timothy Receveur, Apex, NC (US); Eugene Urrutia, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 229 days.

(21) Appl. No.: 17/153,073

(22) Filed: Jan. 20, 2021

(65) Prior Publication Data

US 2021/0219873 A1 Jul. 22, 2021

Related U.S. Application Data

(60) Provisional application No. 62/963,810, filed on Jan. 21, 2020.

(51) Int. Cl.
*A61B 5/11* (2006.01)
*A61B 5/00* (2006.01)

(52) U.S. Cl.
CPC .......... *A61B 5/1117* (2013.01); *A61B 5/1115* (2013.01); *A61B 5/4806* (2013.01); *A61B 5/7264* (2013.01); *A61B 5/747* (2013.01)

(58) Field of Classification Search
None
See application file for complete search history.

(56) References Cited

U.S. PATENT DOCUMENTS

| 7,369,680 | B2 | 5/2008 | Trajkovic et al. |
| 9,501,919 | B2 | 11/2016 | Aett et al. |
| 9,728,061 | B2 | 8/2017 | Shen et al. |
| 10,058,272 | B2 | 8/2018 | Heinrich et al. |
| 10,262,517 | B2 | 4/2019 | Bobda |
| 10,276,019 | B2 | 4/2019 | Johnson et al. |

(Continued)

FOREIGN PATENT DOCUMENTS

| CN | 107103733 B | 7/2019 |
| JP | 2018067203 A | 4/2018 |

(Continued)

OTHER PUBLICATIONS

Chang et al., "In-Bed Patient Motion and Pose Analysis Using Depth Videos for Pressure Ulcer Prevention," IEEE International Conference on Image Processing (ICIP), pp. 4118-4122 (2017).

(Continued)

*Primary Examiner* — Devin B Henson
*Assistant Examiner* — Matthew Eric Ogles
(74) *Attorney, Agent, or Firm* — Merchant & Gould P.C.

(57) ABSTRACT

Monitoring patients utilizing computer vision to analyze patient movements on or near a patient support apparatus such as a bed. Computer vision is employed to analyze video feed of patients to detect movements indicative of clinical parameters. Information generated by the computer vision processor can be recorded to a patient's electronic medical record. Such information can be used to make clinical assessments, diagnoses, or detect critical patient events requiring attention of caregivers. In instances where caregiver assistance is required, an alert can be communicated to one or more caregivers through a caregiver call system.

16 Claims, 5 Drawing Sheets

(56) References Cited

U.S. PATENT DOCUMENTS

| | | | |
|---|---|---|---|
| 10,304,184 B2 | 5/2019 | Nabatame et al. | |
| 10,319,209 B2 | 6/2019 | Foss | |
| 10,388,016 B2 | 8/2019 | Kusens et al. | |
| 2012/0026308 A1* | 2/2012 | Johnson | G06V 20/40 348/E7.085 |
| 2012/0140068 A1 | 6/2012 | Monroe et al. | |
| 2013/0246088 A1* | 9/2013 | Huster | G06Q 10/0635 705/2 |
| 2015/0109442 A1* | 4/2015 | Derenne | H04N 7/185 348/143 |
| 2018/0068179 A1 | 3/2018 | Derenne et al. | |
| 2019/0206218 A1* | 7/2019 | Kusens | H04N 13/204 |
| 2019/0231231 A1 | 8/2019 | Saria et al. | |

FOREIGN PATENT DOCUMENTS

| | | | |
|---|---|---|---|
| JP | 2019527082 A | 9/2019 | |
| WO | 2017146643 A1 | 8/2017 | |
| WO | 2019003859 A1 | 1/2019 | |

OTHER PUBLICATIONS

Electronic health record, Wikipedia, https://en.wikipedia.org/w/index.php?title=Electronic%20health%20-record&oldid=935209047, 22 pages (Jan. 11, 2020).
Extended European Search Report for Application No. 21152777.5 mailed Jun. 10, 2021.
Sebe et al., "Machine Learning in Computer Vision," Springer Netherlands, ProQuest Ebook Central, http://ebook.central.proquest.com/lib/epoebooks/detal.action?docID=303223, 25 pages (2005).

* cited by examiner

MACHINE VISION TO PREDICT CLINICAL PATIENT PARAMETERS

RELATED APPLICATION

The present application claims the benefit of U.S. Patent Application Ser. No. 62/963,810 filed on Jan. 21, 2020, the entirety of which is hereby incorporated by reference.

BACKGROUND

In an ideal world, caregivers in healthcare facilities would be able to observe patients at all times. Various monitoring devices can be employed to record patient vital signs, which can indicate some medical conditions. Nurse call systems can alert caregivers when the patient needs assistance or attention. Sensors in hospital beds can detect patient movements using load cells. However, visual observation of a patient can be the best way to detect some health indications. Visual monitoring of patients can provide information about patient mobility, fall risk, sleep patterns, and risk for developing various medical conditions.

SUMMARY

Embodiments of the disclosure are directed to systems and methods for predicting clinical patient parameters. More particularly, a system including a camera and a computer vision processor are utilized to analyze real-time video feeds of patients in bed to determine if clinical patient parameters are present. In instances where the clinical patient parameters indicate that the patient needs assistance, an alert can be automatically issued to caregivers.

In one aspect, a method of monitoring a patient includes: receiving a video feed of the patient at a patient support apparatus in real-time; analyzing, with a computer vision processor, the video feed to determine one or more postures of the patient relative to the patient support apparatus over time; and determining, based on the one or more postures, one or more clinical parameters of the patient. In some embodiments, the video feed is received from a camera positioned over the patient support apparatus. In some embodiments, the computer vision processor utilizes a machine learning model to analyze the video feed, the machine learning model being trained on video feeds of patients and corresponding indications of clinical parameters from a caregiver.

In another aspect, a patient monitoring system includes a bed configured to support a patient while under medical care; a video camera mounted above the bed; and a patient monitoring computing device comprising a processor and a memory comprising instructions that, when executed, cause the processor to operate a patient monitoring system configured to perform a series of operations. Those operations include: receiving a video feed of a patient at a bed in real-time; extracting, with a computer vision processor, features from the video feed, the features including one or more of patient presence, patient body posture, patient movement over time, and presence of other individuals; and analyzing the features to determine one or more clinical parameters of the patient. In some embodiments, the computer vision processor utilizes a machine learning model trained on video feed data of patients that have been identified by caregivers as having particular clinical patient parameters.

In yet another aspect, one or more computer-readable media having computer-executable instructions embodied thereon that, when executed by one or more computing devices, cause the computing devices to: receive a plurality of video feed images of a plurality of patients at a plurality of patient beds; receive input of conditions identified by caregivers as indicating clinical patient parameters; extract features from the video feed images that are predicted to correspond to the conditions; and output a computer vision model. In some embodiments, the computer-executable instructions further cause the computing devices to: record video images of a patient at a patient bed; analyze the video images using the computer vision model to identify features corresponding to conditions; analyze the conditions to determine clinical patient parameters; record the clinical patient parameters for the patient; and determine whether an alert needs to be issued in response to the clinical patient parameters.

The details of one or more techniques are set forth in the accompanying drawings and the description below. Other features, objects, and advantages of these techniques will be apparent from the description, drawings, and claims.

DETAILED DESCRIPTION

Figure 1:
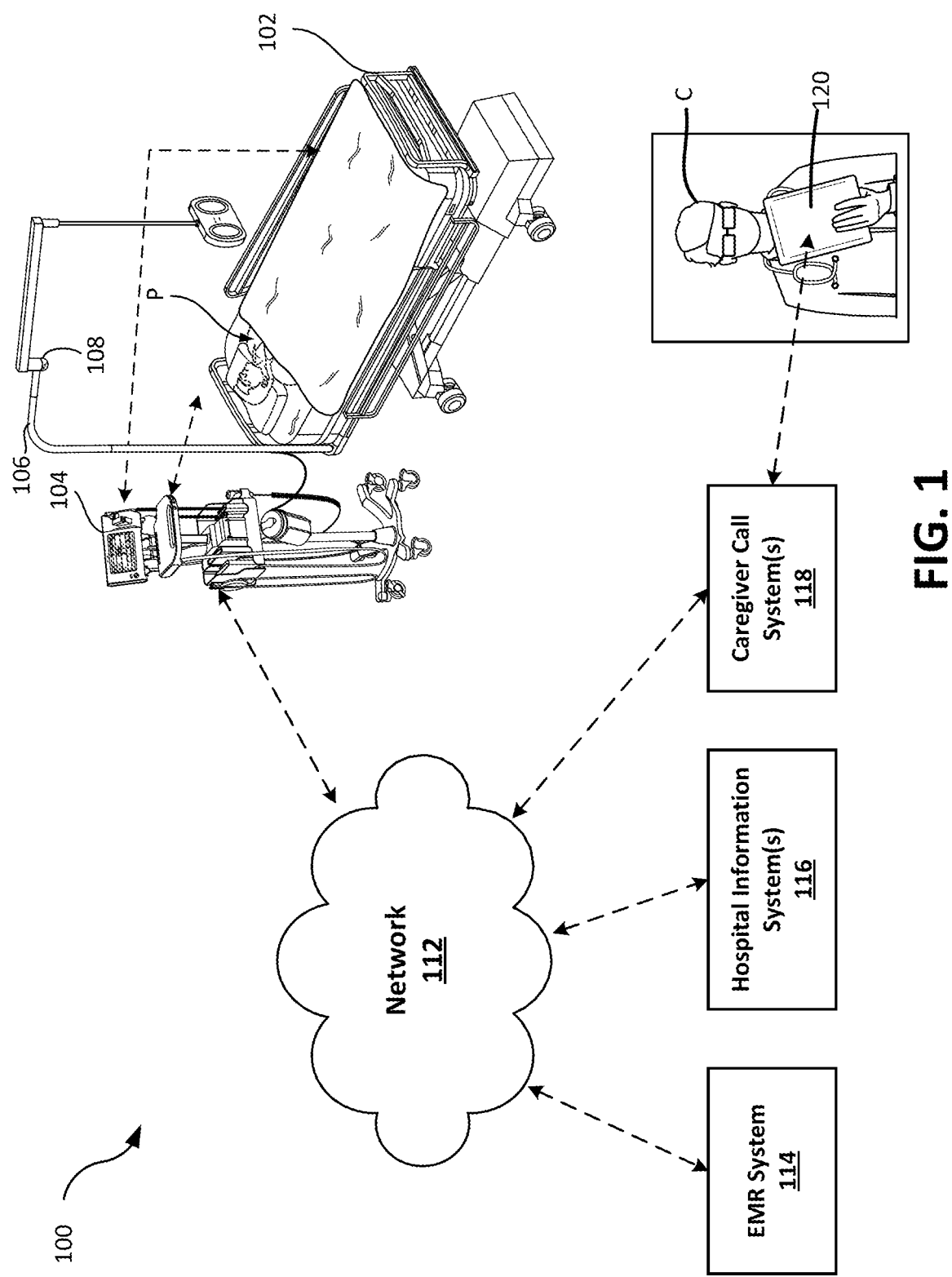
FIG. 1 is a schematic diagram illustrating an example system for monitoring a patient.

The present disclosure is directed to monitoring patients using computer vision. Many patient assessments can be made based on observations of patient movements at or near a patient support apparatus such as a patient bed. Because it is not practical for a caregiver to constantly observe each patient at a healthcare facility, computer vision is employed to analyze video feed of patients to detect movements indicative of clinical parameters. In instances where caregiver assistance is required as the result of those clinical parameters, an alert can be communicated to one or more caregivers.

Caregivers refer to any persons responsible for the care of a patient. Examples of caregivers include physicians, nurses, and other individuals working within a healthcare facility such as a hospital or nursing home. Additionally, caregivers can include family members and other at home caregivers such as friends, home health aides, personal care aides, nurses, and nursing assistants.

Clinical patient parameters refer generally to observable indicators of the state of a patient's health and care. Clinical patient parameters can be inferred from conditions of the patients that are observed visually. Examples of such conditions include how frequently a patient turns in bed to shift weigh to different parts of the body, how often a patient gets out of bed, and how long a patient sleeps. Further details about example patient parameters are provided below.

Clinical Patient Parameters

"Time on Tissue" Detection

The amount of time that a patient's weight puts pressure on a particular part of the body is relevant to the risk of developing pressure injuries. The prediction used to build an inference model for this indication is that being in any one position for too long will lead to pressure injuries. Thus, the amount of time that a patient is on their left side, right side, or in a supine position factors into a determination of the patient having a risk of developing pressure injuries. Video feeds are analyzed with computer vision to determine when a patient is on their left side, right side, or in supine position. The patient's body position is followed over time to determine how long the patient is in any one position.

In one example, the prediction may be that if the patient spends less than a given time in any one position at a time, the risk of developing pressure injuries is low. Conversely, if the patient spends more than a given time in any one position at a time, the risk of developing pressure injuries is high. A response to determining that the risk of developing pressure injuries is high could be to submit an alert to a caregiver to turn the patient so that their body weight is resting on a different part of their body.

Bed Exit Prediction

Two factors can be considered for predicting whether a patient is likely to exit a bed. One is the frequency of previous bed exits. A patient that has exited the bed previously is more likely to do so again. This could be because the patient is capable of getting out of bed and moving about unassisted. This could also be because, even though the patient needs assistance and has been instructed not to get out of bed unassisted, the patient has shown a pattern of stubborn behavior and has still tried to or has gotten out of bed unassisted.

Another factor to consider for predicting bed exits is the sequence and timing of body postures of a patient that indicate the patient is preparing to exit the bed. Body postures can be determined from video feeds of patients on a bed using human pose estimation machine learning techniques. The timing and sequence of body postures that lead to a bed exit can be determined with a machine learning algorithm. A user can indicate which video feeds result in a bed exit and those videos can be used to train the machine learning algorithm to detect the movements that lead up to the bed exit.

Sleep Detection

Sleep is essential to human health. Because of its importance, monitoring how much sleep a patient is getting can provide insight to how well a patient is recovering, how much the pain the patient is in, and whether caregivers are interrupting patient sleep too often. The condition of a patient sleeping can be detected by assessing the patient body posture and how often the patient moves. This could be aided by information such as respiration rate and heart rate.

Mobility Detection

Measuring patient mobility is important for assessing progress in recovery and rehabilitation of patients. The earlier a patient can start moving about, the faster their recovery will be. Early mobility programs have been shown to reduce lengths of patient stays at healthcare facility and improved patient outcomes.

Various assessments are used by caregivers to determine a patient's level of mobility. For example, the timed up and go test (TUG) assesses a patient's mobility based on their ability to rise from a seated position, walk about three meters, turn around, and walk back to sit down within a given period of time (usually about 12 seconds). Computer vision can be used to automatically record patients getting out of bed and walking across the room. The data recorded from video images of the patient can be recorded in the patient's EMR for future use by caregivers.

Determining patient postures while on the bed can also aid in determining a patient's level of mobility for purposes of implementing a progressive mobility program. The amount of time spend in each of a variety of body postures can be assessed from computer vision analysis of video feeds of the patient.

Fall Detection

Computer vision can be used to analyze video feeds to determine when a patient has fallen. The patient could have fallen out of bed or fell after trying to exit the bed unassisted. Analyzing the video feed to determine that the patient is not in the bed and determining that the patient's body posture indicates that the patient is not standing upright, but on the ground triggers a determination that the clinical patient parameter of a fall has occurred. In some embodiments, additional information from, for example, load sensors in the patient bed can further confirm that a fall has occurred. Generally, a finding that a fall has occurred will result in an alert automatically being issued to one or more caregivers to come assist the patient immediately.

Pressure Injuries

Pressure injuries are a common and serious problem for patients in healthcare facilities. These complications can delay patient recovery and increase cost of care of the patient. Various factors can contribute to the development of skin ulcers and deep tissue injuries. The Braden Scale is an assessment used by caregivers to determine a patient's risk of developing pressure ulcers. Six criteria are examined in the assessment: 1) sensory perception, 2) moisture, 3) activity, 4) mobility, 5) nutrition, and 6) friction and shear. Three out of the six of these criteria can be assessed automatically using computer vision.

Activity and mobility can be assessed by determining how often a patient moves in bed based on identifying changes in patient posture. Additionally, the frequency of patient exits from the patient can inform this determination. The friction and shear criteria can be assessed in part by how frequently the patient pulls up in bed. The friction of the patient's skin pulling across the bed as his or her body is pulled across it can increase the risk of developing pressure injuries. This is true regardless of whether the patient is doing this with or without the aid of a caregiver.

Detection of Other People

The computer vision processor can use object recognition and object detection to determine that an individual other than the patient is near the patient bed. In some instances, the individual is a caregiver. The presence of a caregiver can be further confirmed with location sensors on the person of the caregiver. Caregiver presence can be used to determine whether healthcare facility compliance metrics are being met. The actions that the caregiver is taking with the patient could be determined from entries received in the patient's EMR or adjustments detected by vitals sign monitors.

In some instances the computer vision processor can determine whether another individual is on the bed with the patient. This information can be used to distinguish when signals from other devices are being caused by someone other than the patient. For example, a change in the weight detected by load sensors in the patient bed could be determined to be caused by another person on the bed when the computer vision processor identifies that another individual is present.

The disclosed embodiments provide technical advantages over existing solutions for monitoring patients. Visual observations of patients are automated using computer vision. The computer vision processor is programmed to recognize features indicative of patient parameters. Automation reduces the amount of time that caregivers need to spend observing patients and improves the accuracy of monitoring over systems that rely on vitals monitors alone. Additionally, when patient parameters are detected, they can be analyzed in combination with patient data to determine if alerts need to be issued. The alerts can be automated, making the entire process of observing patient movements and responding to patient needs more efficient.

FIG. 1 is a schematic diagram illustrating a patient monitoring system 100. The system 100 can be implemented, for example, at a hospital, clinic, or other healthcare facility. In the example of FIG. 1, the patient monitoring system 100 includes a patient bed 102 in communication with a patient monitoring computing device 104. The patient bed 102 is configured to support a patient P and is equipped with an attachment mount 106 having a camera 108 mounted thereon. A patient monitoring computing device 104 communicates via a network 112 with other computing systems including an electronic medical record (EMR) system 114, a hospital information system 116, and a caregiver call system 118. The caregiver call system 118 communicates with one or more caregivers C via caregiver computing devices 120.

The patient bed 102 operates to provide a surface for a patient P to rest upon while under medical care. The patient bed 102 could alternatively be a chair, reclining chair, or adjustable bed. While the present disclosure is not limited to any particular patient support apparatus, a bed will be used as an example throughout for convenience. In some embodiments, the patient bed 102 is a smart bed equipped with a memory device and a processing device. The smart bed can include various functionalities to monitor a patient, entertain a patient, and make a patient more comfortable.

In some embodiments, the patient bed 102 is in communication with one or more patient monitoring devices via wireless or wired connections. In some embodiments, the patient bed 102 includes load sensors and/or motion sensors to monitor patient movements on the bed. One example of a smart hospital bed is the Advanta™ 2 Med Surg Bed manufactured by Hill-Rom® of Batesville, Indiana.

In some embodiments, the patient bed 102 is equipped with an attachment mount 106. In some embodiments, the attachment mount 106 has a video camera 108 mounted thereon. In some embodiments, the camera is a video camera having at least a 120 degree field of view. In some embodiments, the field of view is at least 150 degrees or at least 180 degrees. In some embodiments, the camera is a fish-eye type camera that provide a 360 degree field of view.

In some embodiments, the camera communicates with other computing devices wirelessly. In other embodiments, the camera is wired into a power and communication system within the healthcare facility. In some embodiments, the video camera provides a real-time video feed in high definition. In some embodiments, the video camera records images using visible light. In some embodiments, the video camera can utilize other technologies such as radar, infrared, LIDAR, and magnetic resonance images.

Generally, visible light cameras operate at rate of about 30 frames per second. In some embodiments, the video cameras record less than 30 frames per second. In some embodiments, the video cameras record greater than 30 frames per second. In some embodiments, the video cameras record 60 frames per second or greater. One example of a camera that could be used with this monitoring system is the D-Link DCS-6315 Network Camera.

The video camera 108 is positioned such that a video feed recorded by the camera 108 captures the entire patient bed 102 as well as the immediate surrounding area. The video feed is analyzed by the patient monitoring device 104. However, in other embodiments, the video feed can be analyzed at the patient bed 102 or at a computing device integrated with the video camera 108.

In some embodiments, the attachment mount 106 has device attached to it that can be used by the patient. This could be a small computing device with a display that is hung from the attachment mount 106 over the patient bed 102, as shown in FIG. 1. In some embodiments, this device can provide a control panel with a reading light, patient remote, personal device holder, and USB port. An example of such a device is the Experience Pod™ device integrated into the Centrella™ Smart Bed manufactured by Hill-Rom®.

The patient monitoring computing device 104 operates to receive and record data for a particular patient from one or more patient monitoring devices. The patient monitoring devices are in communication with the patient monitoring computing device 104 through a wired or wireless connection. Examples of patient monitoring devices include heart rate monitors, pulse oximeters, etc. In some embodiments, the patient monitoring devices can include the patient bed 102 itself. In the example of FIG. 1, the patient monitoring computing device 104 can also receive and analyze video feeds received from the video camera 108. In some embodiments, the video feed is communicated directly to the patient monitoring computing device 104. In other embodiments, the video feed is communicated first to the patient bed 102.

In some embodiments, the patient monitoring computing device 104 includes a processor and memory device. The memory device can include instructions for the processor to analyze data received from patient monitoring devices. In some embodiments, the memory device can also store patient data locally. The patient monitoring computing device 104 can include a display and a user interface face which allows a caregiver to easily access patient data as well as input data into a patient's EMR. In some embodiments, patient monitoring computing device 104 communicates patient data to one or more of the patient monitoring device 104, EMR system 114, hospital information system 116, and caregiver call system 118 through the network 112. The patient monitoring computing device 104 can also include one or more input devices such as a keyboard, mouse, or touchscreen that receives input from a caregiver or other user.

The patient monitoring device 104 operates on the patient monitoring computing device 104. In some embodiments, the patient monitoring device 104 is hosted on a remote server that is accessed by the patient monitoring computing device 104 through the network 112. In some embodiments, one or more components of the patient monitoring device 104 operate within the patient bed 102 if the patient bed is equipped with a processing device. The patient monitoring device 104 is described in greater detail in FIG. 2.

The network 112 operates to mediate communication of data between network-enabled computing systems. In various embodiments, the network 112 includes various types of communication links. For example, the network 112 can include wired and/or wireless links, including cellular, Bluetooth, ultra-wideband (UWB), 802.11, ZigBee, and other types of wireless links. The network 112 can include one or more routers, switches, mobile access points, bridges, hubs, intrusion detection devices, storage devices, standalone server devices, blade server devices, sensors, desktop computers, firewall devices, laptop computers, handheld computers, mobile telephones, vehicular computing devices, and other types of computing devices.

The electronic medical record (EMR) system 114 operates to record information relevant to the medical history of each patient. Examples of information that might be stored in a patient's EMR includes lab results, surgical history, family medical history, current medications, and previous medical diagnoses. A patient's fall risk score (as determined by e.g. Morse Fall Scale, Johns Hopkins Fall Risk Assessment Tool, etc.) or sub-score (as determined by Get Up and Go test) are other pieces of information that could be added to an EMR. In some embodiments, information gathered by the patient monitoring device 104, such as information about patient movements, could be recorded in the patient's EMR. Examples of electronic medical records systems 114 include those developed and managed by Epic Systems Corporation, Cerner Corporation, Allscripts, and Medical Information Technology, Inc. (Meditech).

The hospital information systems 116 operate to record, store, and communicate information about patients, caregivers, and hospital facilities. Hospital information systems 116 generally handle administrative information for a hospital or clinic. Examples of hospital information systems 116 include admit/discharge/transfer (ADT) systems, laboratory information systems (LIS), and clinical decision support (CDS) systems.

The caregiver call systems 118 operate to generate alerts that are triggered by one or more rules. The alerts are disseminated to caregivers that need to perform critical tasks. The alerts can be generated based on data from the vital signs monitoring devices or updates to patient information that are received at the EMR system 114. As an illustrative example, patient movements indicative of a particular clinical patient parameter can trigger an alert from the caregiver call system 118 which is then sent to a computing device 120 associated with a caregiver C so that the caregiver C is notified of the need to perform critical tasks based on the clinical patient parameter. In the example of FIG. 1, the caregiver C is a nurse operating a tablet computing device 120. Other examples of computing devices 120 include smartphones, desktop computers, laptops, pagers, and other network enabled devices. In some embodiments, the alert is delivered in any suitable form, including audible, visual, and textual forms such as a message on a display or a pager message.

Figure 2:
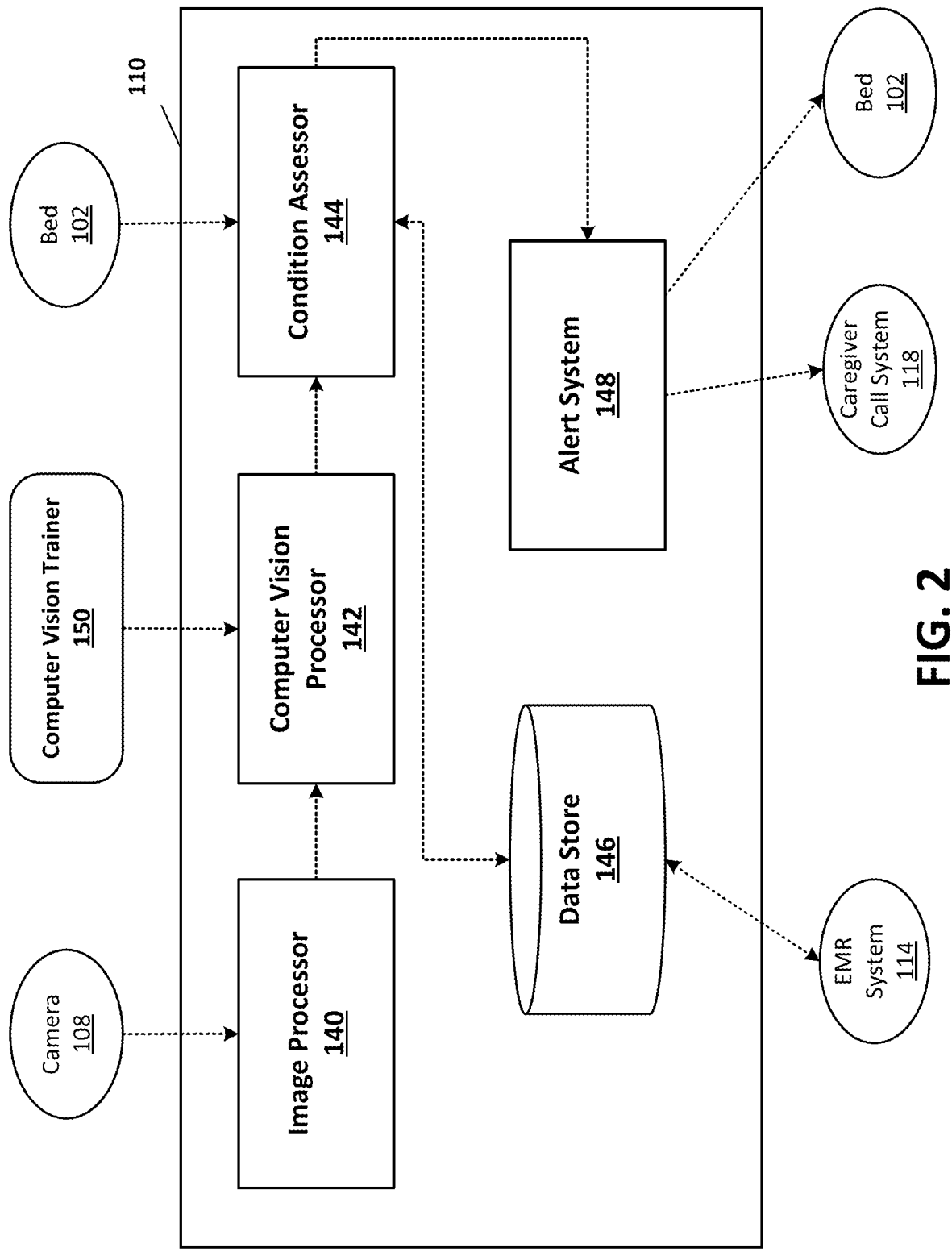
FIG. 2 is a detailed schematic diagram illustrating the patient monitoring system of FIG. 1.

FIG. 2 is a more detailed schematic diagram of the patient monitoring device 104 of FIG. 1. In some embodiments, the patient monitoring device 104 operates on the patient monitoring computing device 104. In other embodiments, the patient monitoring device 104 operates on a remote server that is in communication with one or more patient monitoring devices. In the example of FIG. 2, the patient monitoring device 104 includes an image processor 140, a computer vision processor 142, a condition assessor 144, a data store 146, an alert system 148, and a computer vision trainer 150.

The image processor 140 operates to receive video feeds from one or more cameras 108. Initial processing of the images is performed by the image processor 140 to prepare the images for further analysis by the computer vision processor 142. Initial processing of the video images can include ensuring that an image coordinate system is properly applied to the images, reducing noise, and otherwise normalizing properties of the image to ensure that it can be properly processed by the computer vision processor 142.

The computer vision processor 142 operates to analyze the images to extract features needed for the condition assessor 144 to determine if a clinical patient parameter is present. In some embodiments, features relate to patient postures, presence, and movements indicative of medical conditions, patient mobility, sleep patterns, and the like. As described in more detail above, some examples of features include amount of time a patient spends in one position on the bed, sequences of movements indicating impending bed exit, and presence of a caregiver near the bed. The computer vision processor 142 utilizes algorithms and models trained on sample data by the computer vision trainer 150.

There are multiple methods, techniques, models, and algorithms that can be employed in computer vision. Analyses performed by the computer vision processor 142 can include object identification (is that the patient?), object verification (is there someone at the bed?), object landmark detection (where is the patient in relation to the bed?), object segmentation (which pixels belong to an object in the image), and recognition (is that the patient and where are they?).

Examples of algorithms that can be utilized in object recognition include scale-invariant feature transform (SIFT) and convolutional neural networks (CNN). Examples of algorithms that can be utilized in motion analysis include region-based convolutional neural networks (R-CNN) and stacked auto encoder (SAE). Techniques such human pose estimation and object tracking can improve the accuracy of the computer vision processor 142 in determining how a patient is moving and how a patient is positioned at a patient bed.

The condition assessor 144 analyzes the features identified by the computer vision processor 142 to determine patient postures and movements that indicate clinical patient parameters. The condition assessor 144 can also draw upon patient information from the data store 146 and/or the patient bed 102. In some embodiments, the condition assessor 144 directly draws upon information from the EMR system 114.

The computer vision trainer 150 operates to train machine learning algorithms that are employed by the computer vision processor 142. Training data comprises video feed labeled with corresponding clinical patient parameters.

The data store 146 operates to store data processed by the image processor 140 and computer vision processor 142. In some embodiments, the data store 146 temporarily stores data from the EMR system 114. Information in the data store 146 can be communicated to the EMR system 114. In some instances, patient information is received from the EMR system 114 and used to process the video feeds to determine whether a particular patient parameter is occurring. The EMR information in combination with the machine vision analysis can be used in combination by the condition assessor 144 for assessing whether an alert needs to be issued for the patient.

The alert system 148 operates to communicate alarms or alerts to computing systems in communication with the patient monitoring computing device 104 or patient bed 102. For example, the alert system 148 can communicate alerts to caregiver call systems 118 to notify caregivers of clinical indications detected by the computer vision processor 142. The alerts can be disseminated to a status board or caregiver mobile devices. The alert system 158 can also activate an alert response at the patient bed 102. If the patient bed 102 is equipped with safety devices to mitigate falls, those devices can be automatically activated. The alert system 158 can also communicate a visual or audible alert at the patient monitoring computing device 104 or bed 102. In some embodiments, the alert at the patient bed instructs the patient to stay in bed or to wait for a caregiver to arrive. This alert could be a voice command delivered over a speaker at the patient bed 102 or placed elsewhere near the patient bed.

In some embodiments, the result of the computer vision analysis is a modified video feed provided to a centralized monitoring station. In some embodiments, a video display of a computing device displays video image feeds of the area surrounding and including the patient bed. In some embodiments, multiple video image feeds are monitored by a caregiver at the centralized monitoring station. Each video feed is of a different patient bed area. In some embodiments, each video feed is displayed on a separate video display. In other embodiments, multiple video feeds are displayed on one video display in a split screen mode.

In some embodiments, the processed image data is a video feed that is highlighted in one color or a combination of colors to indicate that caregiver attention is needed for the patient in the video feed. In some embodiments, the alert system 148 processes information received form the condition assessor 144 to determine when all or a portion of a video feed should be highlighted. In some embodiments, the caregiver monitoring the video feeds will alert another caregiver to assist the patient when a highlighted video feed is observed. The highlighted video feeds make it easier for one caregiver to monitor multiple patients at a time.

In some embodiments, alerts are generated automatically based on the patient conditions determined from analyzing the video feeds. In some embodiments, the alerts are generated automatically by the alert system 148 in response to particular inputs received form the condition assessor 144.

Alerts can be communicated to caregivers through various means. In some embodiments, the alerts are delivered to a computing device associated with the caregiver in the form of a text message, a pager message, an email, a phone call, or a push notification. In some embodiments, the alerts are communicate to a display of a computing device at the patient bed or in the patient's hospital room. In some embodiments, alerts are presented on larger displays in general common areas of the healthcare facility. For example, the larger display could be near to a caregiver, such as at a nurses station in a hospital or skilled nursing facility. In some embodiments, alerts can be communicated to caregivers through projecting colored light or images in the patient's room or near the patient's bed to indicate to passing by caregivers that action is needed for the patient.

Alerts can also be communicated to the patient to reminder the patient to take particular precautions or provide instructions to the patient in response to the movements detected by the patient monitoring device 104. In some embodiments, the alert could be communicated to the patient bed or the patient monitoring computing device 104 in the form of a visual and/or audio message. In some embodiments, the alert could be communicated over a microphone/intercom system in the patient's room. In some embodiments, alerts are communicated to devices or components within the patient's room or on the patient's bed. For example, a fall risk alert could automatically trigger guard rails to raise on the bed.

Figure 3:
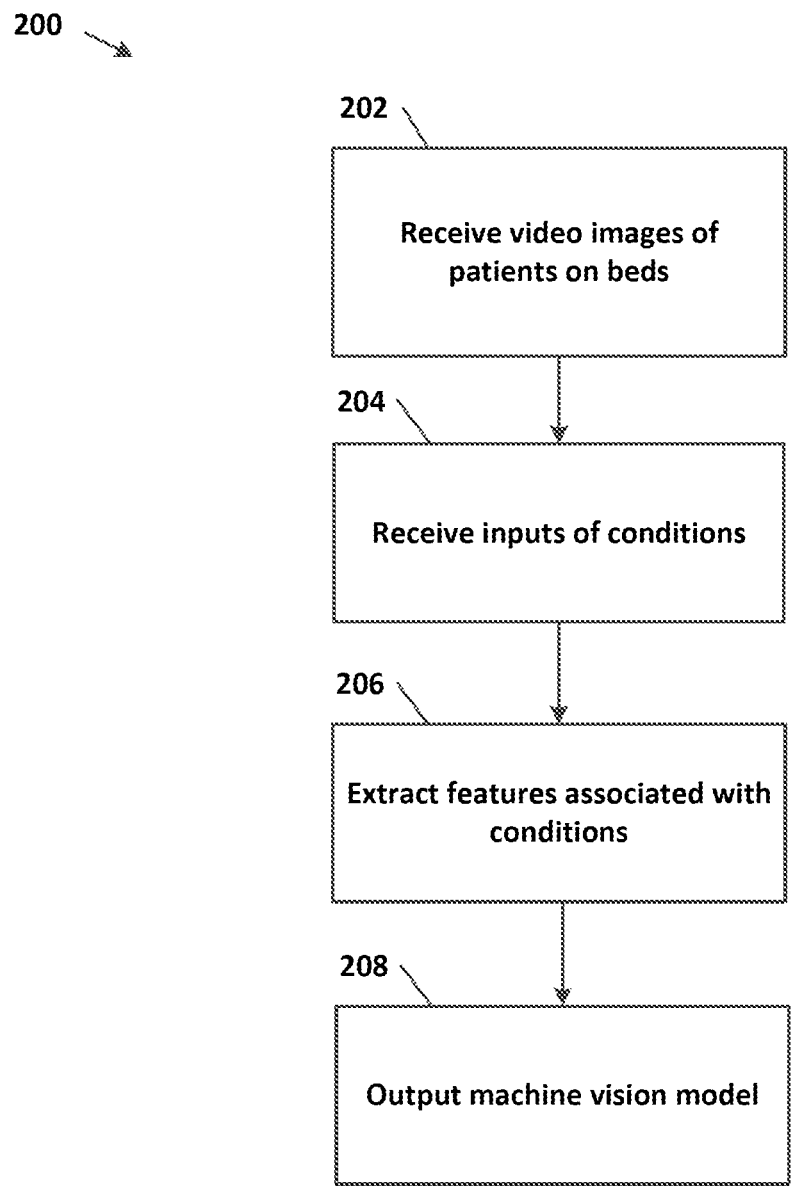
FIG. 3 is a flow chart illustrating an example method of training a computer vision system.

FIG. 3 is a flow chart illustrating an example method 200 of training a computer vision processor to recognize clinical patient parameters at a bed. In some embodiments, this method 200 is performed by the computer vision trainer 150 of FIG. 2.

At operation 202, video images of patients on or near patient beds are received. In some embodiments, the video images are received from video feed recorded by a camera 108 mounted on or near the patient bed 102 such that the camera can record the area including the bed 102 and the area immediately surrounding the bed 102.

At operation 204, inputs of conditions are received. Conditions are observable signs of clinical parameters such as body postures, patient presence at the bed, movement patterns, and timing. Conditions are determined by caregivers based on observations of patient movements in the videos. Hypotheses about observable conditions are used to identify potential features that could be correlated with particular clinical patient parameters. For example, the hypotheses could be that observations of the time that a patient spends in a supine position, on their left side, and on their right side could correlate to patient turn or "time on tissue" detection. The patient turn clinical parameter is used to determine whether a patient is at risk for developing pressure injuries.

At operation 206, features associated with the conditions are extracted. Machine learning algorithms are used to determine the features. Articulation angles of the bed can be used as a reference point. One example of a feature is determining a patient body posture that shows the patient is on their side without changing position for longer than a particular amount of time.

At operation 208, a computer vision model is output. In some embodiments, this computer vision model is used by the computer vision processor 142 of FIG. 2 to analyze processed video feeds of patients to determine if a patient clinical parameter is present.

There are multiple methods, techniques, models, and algorithms that can be employed in computer vision. Two key capabilities that the computer vision processor 142 must have are object recognition and motion analysis. Examples of algorithms that can be utilized in object recognition include scale-invariant feature transform (SIFT) and convolutional neural networks (CNN). Examples of algorithms that can be utilized in motion analysis include region-based convolutional neural networks (R-CNN) and stacked auto encoder (SAE). Techniques such human pose estimation and object tracking can improve the accuracy of the computer vision processor 142 in determining how a patient is moving and how a patient is positioned at a patient bed.

In some embodiments, the computer vision model is validated using additional sets of video feed data. In some embodiments, the computer vision model is updated as it is used and feedback is received from caregivers about clinical parameters that are observed.

Figure 4:
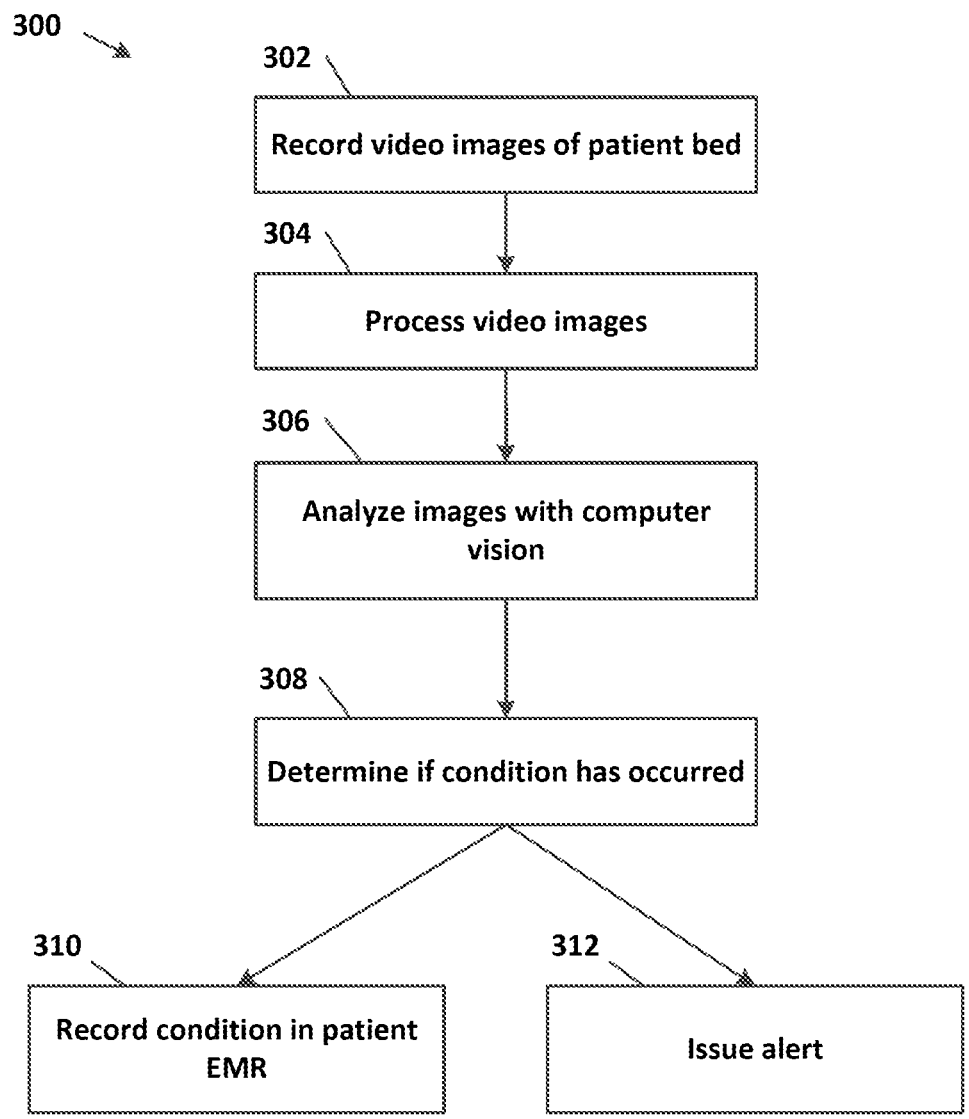
FIG. 4 is a flow chart illustrating an example method of monitoring a patient using a computer vision system.

FIG. 4 illustrates a flow chart of an example method 300 of monitoring a patient to predict clinical patient parameters. In some embodiments, this method 300 is performed by the patient monitoring device 104 of FIGS. 1 and 2.

At operation 302, images of a patient at a bed are recorded. In some embodiments, a video camera, such as the camera 108 of FIG. 1 records video feeds of a patient on a bed 102 in real-time. Preferably, the video feed covers an area immediately surrounding the bed as well in order to capture patient movements when the patient is not in the bed. For example, if the patient should happen to fall out of the bed, the video camera would be able to capture images of that event.

At operation 304, the video images are processed. In some embodiments, the image processor 140 performs initial processing steps on the video feed as it is received in real-time. The initial processing steps could include normalizing the images, reducing noise, and validating the coordinate system applied to the images.

At operation 306, the processed images are analyzed with computer vision. In some embodiments, this is performed by the computer vision processor 142 of FIG. 2. In some embodiments, the computer vision processor 142 employs one or more machine learning algorithms or models trained for computer vision processing of real-time video feeds of patients to determine patient body postures and patterns of movement. In some embodiments, the algorithms also determine patient presence at the bed as well as the presence of other individuals near the bed. These determinations are derived from features that are extracted from the video images by the machine learning algorithms.

At operation 308, the features extracted by the computer vision processor 142 are analyzed to determine whether a condition has occurred with the patient at the bed. In some embodiments, the conditions are defined by caregiver input to the patient monitoring device 104 during setup. As mentioned above, conditions are observable signs of clinical parameters such as body postures, patient presence at the bed, movement patterns, and timing of movements. In some embodiments, operation 308 is performed by the condition assessor 144 of FIG. 2.

At operation 310, any conditions detected by the computer vision processor are recorded in the patient's EMR. Generally, any conditions detected could be recorded in the EMR system 114 for future reference by caregivers. In some embodiments, the conditions are at least temporarily stored in the data store 146 before being communicated to the EMR system 114.

At operation 312, an alert is issued in response to the detected conditions. In some embodiments, only certain conditions will trigger an alert. For example, the condition of a patient fall or an anticipated bed exit could trigger an alert to a caregiver to assist a patient. The condition of sleeping might not trigger an alert, but simply be recorded in the patient's EMR. In some embodiments, the conditions are at least temporarily stored in the data store 146 before being used to trigger an alert 148. In some embodiments, the determination of whether an alert should be issued is determined by the condition assessor 144. In other embodiments, the alert system 148 assesses the need for an alert.

In some embodiments, the determination to issue an alert is based on additional information obtained from other patient monitoring devices. In some embodiments, the additional information is temporarily stored in the data store 146 for access by the condition assessor 144 and alert system 148. In some embodiments, data from the patient's EMR is accessed from the EMR system 114 to provide additional information needed to determine whether an alert needs to be issued for a patient. For example, if the patient's EMR indicates that the patient has a high fall risk score, an alert will be issued if the condition assessor 144 determines that the patient is about to exit the bed unassisted. However, if the patient's EMR indicates a low fall risk score, an alert will not be issued when the patient is about to exit the bed unassisted.

Figure 5:
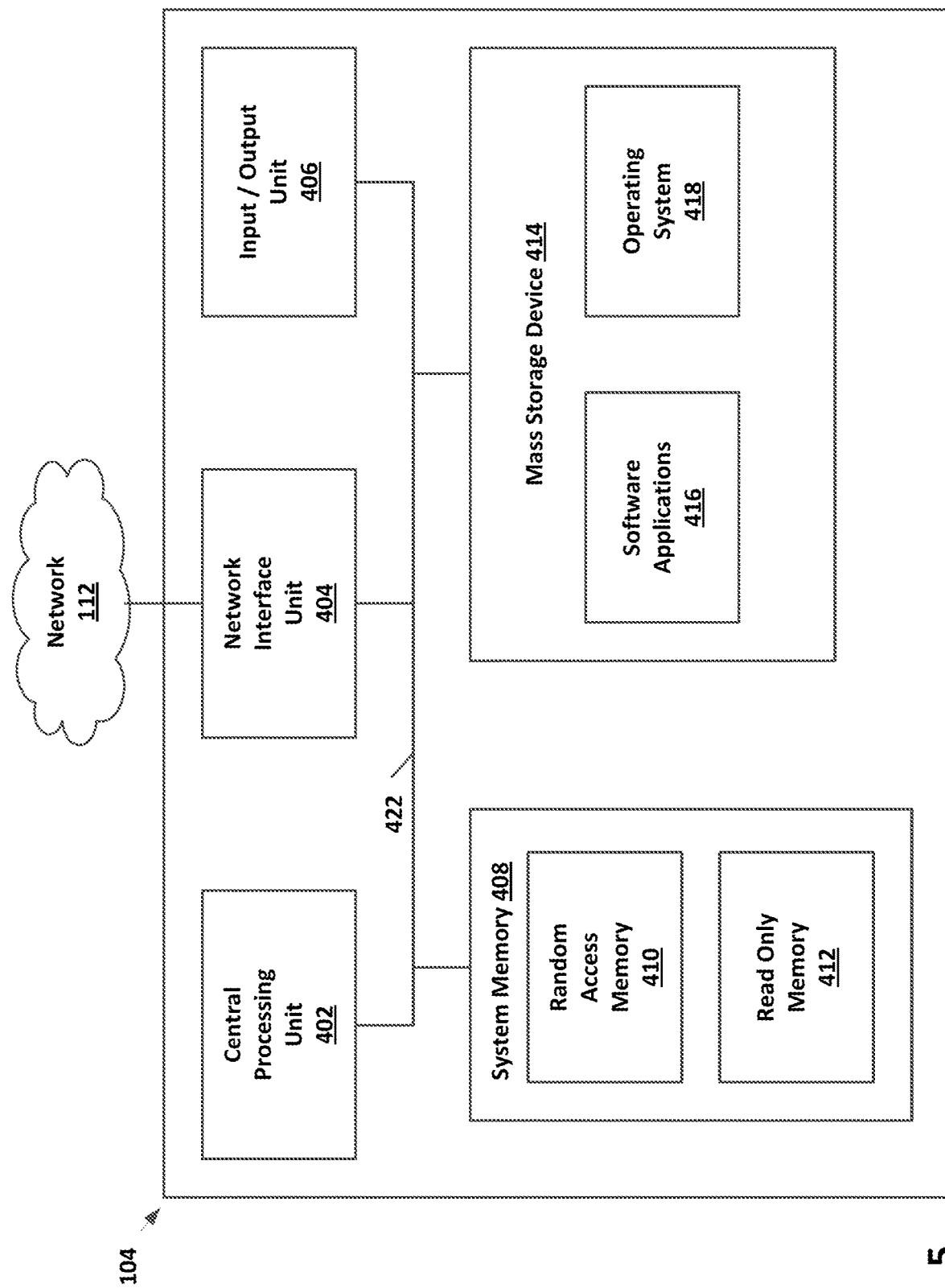
FIG. 5 is a block diagram illustrating example components of a patient monitoring device usable in the system of FIG. 1.

FIG. 5 is a block diagram illustrating an example of the physical components of the patient monitoring device 104. The patient monitoring device 104 could be implemented in various aspects of the system 100 for monitoring a patient. Components of the patient monitoring device 104 can also be incorporated into other devices described herein, such as a computing device integrated into the bed 102. Further, the components illustrated in FIG. 5 could also be used in other systems, such as the EMR system 114, the HIS 116, and/or the caregiver call system(s) 118.

In the example shown in FIG. 5, the patient monitoring device 104 includes at least one central processing unit ("CPU") 402, a system memory 408, and a system bus 422 that couples the system memory 408 to the CPU 402. The system memory 408 includes a random access memory ("RAM") 410 and a read-only memory ("ROM") 412. A basic input/output system that contains the basic routines that help to transfer information between elements within the patient monitoring device 104, such as during startup, is stored in the ROM 412. The computing system 400 further includes a mass storage device 414. The mass storage device 414 is able to store software instructions and data.

The mass storage device 414 is connected to the CPU 402 through a mass storage controller (not shown) connected to the system bus 422. The mass storage device 414 and its associated computer-readable storage media provide non-volatile, non-transitory data storage for the patient monitoring device 104. Although the description of computer-readable storage media contained herein refers to a mass storage device, such as a hard disk or solid state disk, it should be appreciated by those skilled in the art that computer-readable data storage media can include any available tangible, physical device or article of manufacture from which the CPU 402 can read data and/or instructions. In certain embodiments, the computer-readable storage media comprises entirely non-transitory media.

Computer-readable storage media includes volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the patient monitoring device 104.

According to various embodiments, the patient monitoring device 104 can operate in a networked environment using logical connections to remote network devices through a network 112, such as a wireless network, the Internet, or another type of network. The patient monitoring device 104 may connect to the network 112 through a network interface unit 404 connected to the system bus 422. It should be appreciated that the network interface unit 404 may also be utilized to connect to other types of networks and remote computing systems. The patient monitoring device 104 also includes an input/output controller 406 for receiving and processing input from a number of other devices, including a touch user interface display screen, or another type of input device. Similarly, the input/output controller 406 may provide output to a touch user interface display screen or other type of output device.

As mentioned briefly above, the mass storage device 414 and the RAM 410 of the patient monitoring device 104 can store software instructions and data. The software instructions include an operating system 418 suitable for controlling the operation of the patient monitoring device 104. The mass storage device 414 and/or the RAM 410 also store software instructions, that when executed by the CPU 402, cause the patient monitoring device 104 to provide the functionality discussed in this document. For example, the mass storage device 414 and/or the RAM 410 can store software instructions that, when executed by the CPU 402, cause the computing system 400 to monitor a patient on a bed by analyzing video feeds of the patient. The mass storage device 414 includes software applications 416.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method of monitoring a patient, the method comprising:
receiving, with a computer vision processor, a video feed of the patient from a video camera at a patient support apparatus in real-time;
analyzing, with the computer vision processor, the video feed to determine one or more postures of the patient relative to the patient support apparatus over time; and
determining, based on the one or more postures, one or more clinical parameters of the patient, wherein the computer vision processor determines how long the patient has been in one position and detects a clinical parameter of sleep of the one or more clinical parameters of the patient when the patient is stationary for a minimum amount of time on the patient support apparatus, wherein the computer vision processor determines how frequently the patient exits the patient support apparatus to detect a clinical parameter of activity of the one or more clinical parameters of the patient, and wherein the computer vision processor determines how often the patient pulls up in the patient support apparatus to detect a clinical parameter of shear of the one or more clinical parameters of the patient, wherein determining how often the patient pulls up in the patient support apparatus includes identifying changes in the one or more postures of the patient relative to an articulation angle of the patient support apparatus to identify friction between the patient and the patient support apparatus;
determining a shear risk score for the patient indicating the patient's likelihood of developing a pressure injury based on the clinical parameter of sleep of the one or more clinical parameters of the patient, the clinical parameter of activity of the one or more clinical parameters of the patient, and the clinical parameter of shear of the one or more clinical parameters of the patient;
issuing a shear alert when the shear risk score exceeds a threshold value;
determining a fall risk score for the patient, based on the one or more clinical parameters of the patient, indicating the patient's likelihood of falling;
withholding a fall alert when the clinical parameter of sleep is detected;
issuing the fall alert when the fall risk score exceeds a threshold value and the one or more clinical parameters indicate the patient is about to exit the patient support apparatus; and
automatically performing a fall risk mitigation action at the patient support apparatus to prevent the patient from exiting the patient support apparatus.

2. The method of claim 1, wherein the patient support apparatus is a bed and the video feed is received from the video camera mounted to the bed.

3. The method of claim 1, wherein the computer vision processor utilizes a machine learning model to analyze the video feed, the machine learning model being trained on video feeds of patients and corresponding indications of clinical parameters from a caregiver.

4. The method of claim 3, wherein the machine learning model extracts features from the video feed based on the indications corresponding to the clinical parameters.

5. The method of claim 1, wherein the computer vision processor determines how often the patient moves between a supine position, a left side position, and a right side position, and wherein the clinical parameter is "time-on-tissue" detection used to detect a risk of developing pressure injury.

6. The method of claim 1, wherein the computer vision processor determines whether a sequence of positions of the patient indicates a clinical parameter of predicted bed exit of the one or more clinical parameters of the patient.

7. The method of claim 1, wherein the computer vision processor determines when a caregiver is at the patient support apparatus to detect compliance with hospital procedures.

8. The method of claim 1, wherein the computer vision processor determines how often and which positions the patient is on the patient support apparatus to detect a clinical parameter of progressive mobility of the one or more clinical parameters of the patient.

9. The method of claim 1, wherein the computer vision processor determines whether the patient is on a floor next to the patient support apparatus to detect the one or more clinical parameters of a fall.

10. The method of claim 1, wherein the computer vision processor determines when an additional person other than the patient is on the patient support apparatus.

11. The method of claim 1, wherein the computer vision processor determines how frequently the patient moves in the patient support apparatus to detect a clinical parameter of mobility of the one or more clinical parameters of the patient.

12. A patient monitoring system comprising:
a bed configured to support a patient while under medical care;
a video camera mounted above the bed;
a patient monitoring computing device comprising a computer vision processor and a memory comprising instructions that, when executed, cause the computer vision processor to operate the patient monitoring system configured to perform a series of operations comprising:
receiving a video feed of the patient at the bed in real-time;
extracting, with the computer vision processor, features from the video feed, the features including one or more of patient presence, patient body posture, patient movement over time, and presence of other individuals; and
analyzing the features to determine one or more clinical parameters of the patient, wherein the computer vision processor determines how long the patient has been in one position and detects a clinical parameter of sleep of the one or more clinical parameters of the patient when the patient is stationary for a minimum amount of time on the bed, and wherein the computer vision processor determines how frequently the patient exits the bed to detect a clinical parameter of activity of the one or more clinical parameters of the patient, and wherein the computer vision processor determines how often the patient pulls up in the bed to detect a clinical parameter of shear of the one or more clinical parameters of the patient, wherein determining how often the patient pulls up in the bed includes identifying changes in the patient body posture relative to an articulation angle of the bed to identify friction between the patient and the bed;

determining a shear risk score for the patient indicating the patient's likelihood of developing a pressure injury based on the clinical parameter of sleep of the one or more clinical parameters of the patient, the clinical parameter of activity of the one or more clinical parameters of the patient, and the clinical parameter of shear of the one or more clinical parameters of the patient;

issuing a shear alert when the shear risk score exceeds a threshold value;

determining a fall risk score for the patient, based on the one or more clinical parameters of the patient, indicating the patient's likelihood of falling;

withholding a fall alert when the clinical parameter of sleep is detected;

issuing the fall alert when the fall risk score exceeds a threshold value and the one or more clinical parameters indicate the patient is about to exit the bed; and automatically performing a fall risk mitigation action at the bed to prevent the patient from exiting the bed.

13. The system of claim 12, wherein the computer vision processor utilizes a machine learning model trained on video feed data of patients that have been identified by caregivers as having particular clinical patient parameters.

14. The system of claim 12, wherein the operations further comprise analyzing one or both of patient electronic medical record data and bed sensor data to determine the one or more clinical parameters of the patient.

15. The system of claim 12, wherein the operations further comprise activating an alert response at the bed in response to determining that the patient has a particular one of the one or more clinical parameters.

16. One or more computer-readable media having computer-executable instructions embodied thereon that, when executed by one or more computing devices, cause the one or more computing devices to:

receive a plurality of video feed images of a plurality of patients at a plurality of patient beds from at least one video camera;

receive input of conditions identified by caregivers as indicating clinical patient parameters;

extract features from the video feed images that are predicted to correspond to the conditions;

output a computer vision model using the one or more computer devices;

record one or more additional video feed images of a patient at a patient bed;

analyze the one or more additional video feed images using the computer vision model to identify the features;

analyze the conditions identified by caregivers to determine the clinical patient parameters, including to:

determine how long the patient has been in one position and detecting a clinical parameter of sleep of the one or more clinical parameters of the patient when the patient is stationary for a minimum amount of time on the patient bed; and determine how frequently the patient exits the patient bed to detect a clinical patient parameter of activity of the one or more clinical parameters of the patient;

determine how often the patient pulls up in the patient bed to detect a clinical parameter of shear of the one or more clinical parameters of the patient, wherein determining how often the patient pulls up in the patient bed includes identifying changes in patient posture relative to an articulation angle of the patient bed to identify friction between the patient and the patient bed;

record the clinical patient parameters for the patient;

determine a shear risk score for the patient indicating the patient's likelihood of developing a pressure injury based on the clinical parameter of sleep of the one or more clinical parameters of the patient, the clinical parameter of activity of the one or more clinical parameters of the patient, and the clinical parameter of shear of the one or more clinical parameters of the patient;

determine a fall risk score for the patient, based on the one or more clinical parameters of the patient, indicating the patient's likelihood of falling;

determine whether a fall alert needs to be issued in response to the clinical patient parameters, wherein the fall alert is issued when the fall risk score exceeds a threshold value and the one or more clinical parameters of the patient indicate the patient is about to exit the patient bed, wherein a shear alert is issued when the shear risk score exceeds a threshold value, and wherein the fall alert is withheld when the clinical parameter of sleep of the one or more clinical parameters of the patient is detected; and automatically perform a fall risk mitigation action at the patient bed to prevent the patient from exiting the patient bed.

* * * * *